(12) United States Patent
Lumaque-Steeman

(10) Patent No.: US 10,588,793 B2
(45) Date of Patent: Mar. 17, 2020

(54) URINE ABSORBENT PAD

(71) Applicant: EZ Male Pads, Inc., Long Beach, CA (US)

(72) Inventor: Lorna Mateo Lumaque-Steeman, Moreno Valley, CA (US)

(73) Assignee: EZ Male Pads, Incorporated, Long Beach, CA (US)

( * ) Notice: Subject to any disclaimer, the term of this patent is extended or adjusted under 35 U.S.C. 154(b) by 536 days.

(21) Appl. No.: 14/673,549

(22) Filed: Mar. 30, 2015

(65) Prior Publication Data

US 2016/0008188 A1    Jan. 14, 2016

Related U.S. Application Data

(60) Provisional application No. 61/998,947, filed on Jul. 14, 2014.

(51) Int. Cl.
*A61F 13/56* (2006.01)
*A61F 13/58* (2006.01)
(Continued)

(52) U.S. Cl.
CPC ........ *A61F 13/5616* (2013.01); *A61F 13/471* (2013.01); *A61F 13/58* (2013.01);
(Continued)

(58) Field of Classification Search
CPC ...... A61F 13/56; A61F 13/58; A61F 13/5616; A61F 13/471; A61F 2013/583; A61F 2013/15146
See application file for complete search history.

(56) References Cited

U.S. PATENT DOCUMENTS

| 4,216,773 A | 8/1980 | Ryan |
| 5,891,122 A * | 4/1999 | Coates .............. A61F 13/49004 |
| | | 604/385.04 |

(Continued)

FOREIGN PATENT DOCUMENTS

| JP | H0938127 A | 2/1997 |
| JP | H10-234765 A | 9/1998 |
| JP | 2004-180933 A | 7/2004 |

OTHER PUBLICATIONS

International Search Report dated Aug. 28, 2015 as issued by the International Search Authority (ISA/US) for related PCT international application PCT/US2015/030857 with IFD of May 13, 2015.

(Continued)

*Primary Examiner* — Tatyana Zalukaeva
*Assistant Examiner* — Sara A Sass
(74) *Attorney, Agent, or Firm* — Fulwider Patton LLP

(57) ABSTRACT

A disposable urine trap in the form of a foldable pad that envelops the male genitalia and closes around the organ to form a barrier that prevents urine from escaping the trap. The pad includes an asymmetric pair of wings that are separated by a gap and attached to the main body of the pad. The first wing is preferably rectangular in that the distal angles are substantially right angles with parallel side edges and a perpendicular distal edge, and has a length that exceeds a length of a second wing, which is terminates so that the distal edge of the second wing is angled to form an obtuse and an acute angle with respect to its generally parallel sides.

1 Claim, 20 Drawing Sheets

(51) Int. Cl.
*A61F 13/471* (2006.01)
*A61F 13/15* (2006.01)
(52) U.S. Cl.
CPC .............. *A61F 2013/15146* (2013.01); *A61F 2013/583* (2013.01)

(56) References Cited

U.S. PATENT DOCUMENTS

| | | | | |
|---|---|---|---|---|
| 6,129,719 | A * | 10/2000 | Nozaki | A61F 13/471 604/385.01 |
| 6,209,142 | B1 | 4/2001 | Mattsson | |
| 6,443,934 | B1 * | 9/2002 | Glaug | A61F 13/47254 604/385.04 |
| 7,066,920 | B1 * | 6/2006 | Mula | A61F 13/471 604/349 |
| 2003/0158534 | A1 * | 8/2003 | Niki | A61F 13/471 604/385.25 |
| 2006/0282055 | A1 | 12/2006 | Shiomi et al. | |
| 2012/0197228 | A1 | 8/2012 | Miyake et al. | |
| 2016/0008188 | A1 | 1/2016 | Lumaque-Steeman | |

OTHER PUBLICATIONS

International Search Report for PCT/US2017/025121 filed Mar. 30, 2017.
English translation of Office Action from Japanese Patent Office with prior art search, mailed to Japanese associates dated Apr. 23, 2019.
Philippines Substantive Examination Report.

* cited by examiner

URINE ABSORBENT PAD

CROSS-REFERENCES TO RELATED APPLICATIONS

This application claims priority from U.S. Provisional Patent Application No. 61/998,947, filed Jul. 14, 2014, the contents of which are incorporated by reference herein in its entirety.

BACKGROUND

The present invention relates generally to adult incontinence, and more particularly to a urine absorbent pad designed for a male that provides an easy and convenient manner to more safely replace soiled protective wear than the prior art.

Urinary incontinence (UI) is defined as the involuntary loss of urine. In both men and women, age is a consistently reported risk factor for UI; however, it is not considered a normal consequence of aging. Overall, UI affects up to 30% of community dwelling older adults and more than 50% of nursing home residents. Despite its high prevalence, up to one-half of cases may not be reported because individuals with UI may not seek medical intervention. Embarrassment and the perception that UI is an expected consequence of aging are common factors in the failure to seek a solution or treatment. That reluctance is particularly strong in men, who often deem the problem to be associated with a loss of masculinity.

Urinary incontinence is categorized according to pathophysiology and clinical presentation. The four main categories are (1) stress urinary incontinence (SUI), (2) urge urinary incontinence (UUI), (3) overflow incontinence, and (4) functional incontinence. Mixed types of incontinence are common and may complicate diagnosis and treatment because of overlapping symptoms. Studies have found that UI significantly affects psychological well-being and health care-related quality of life. Urinary incontinence may impair sexual function, restrict activities, interfere with interpersonal relationships, decrease self-esteem, increase caregiver burden, increase financial burden, and cause anxiety or depression. It is a common precipitant of institutionalization in older adults.

Because of current demographic trends, UI is an increasingly common medical and socioeconomic problem. One place where the issue arises with great propensity is nursing homes, where older patients often suffer moderate to severe UI due to a variety of physiological conditions. In men, incontinence is often related to prostate problems or treatments that become exacerbated in the elderly. Certain medical conditions, particularly those affecting the brain or nervous system, such as Alzheimer's, Parkinson's, Dementia, Multiple Sclerosis and brain damage, can also lead to incontinence. This is due to the nerve passageways from the brain becoming damaged. The result can be either an overactive bladder (the need to go often and frequently) or an under-active bladder (ineffective emptying leading to leakage). Diabetes and or a stroke can also bring on incontinence.

With aging, bladder capacity decreases, ability to inhibit urination declines, involuntary bladder contractions (detrusor overactivity) occur more often, and bladder contractility is impaired. Thus, voiding becomes more difficult to postpone and tends to be incomplete. Postvoid residual volume increases in as much as ≤100 mL (normal <50 mL). A weakening of the endopelvic fascia often results as well. In men, the tendency for the prostate to enlarge with age causes the partial obstruction of the urethra, leading to incomplete bladder emptying and strain on the detrusor muscle. These changes occur in many normal, continent elderly males and may facilitate incontinence but do not cause it.

It is important to protect the patient's skin from direct exposure to the urine, particularly over long periods of time when skin can become irritated and infected. Many prior art diapers are constructed such that, even though designed to be folded over in somewhat of an envelope fashion, fail to incorporate an arrangement where the edges of the diaper are aligned, thus often leaving the absorbent layer of the overlapping section exposed to the patient's skin. Then, when the patient evacuates, the urine may progress by capillary action through the absorbent layer of the top layer beyond the edge of the layer contacting the skin, thus exposing urine in that layer directly to the patient's skin, causing irritation.

One challenge associated with male incontinence is the necessity for changing clothing, bedding, and other items that may become soiled due to an incontinence patient. When a disabled patient has voided his urine, the caregiver must remove the patient's clothing and bedding while the patient is in a prone position. This can be challenging to the caregiver, who must lift the patient to remove the clothing and bedding while simultaneously trying to extract the soiled garments and sheets, blankets, etc. If the patient is large or overweight, the problem becomes magnified even greater.

Elderly patients and residents of nursing homes who are immobile or have reduced mobility are at high risk for developing pressure ulcers (bed sores). This condition is made worse if the patient is incontinent because the moisture from urine causes the surface of the skin to become irritated and infected. For this reason, it is important to prevent urine from remaining in contact with the skin for any extended period of time, and that it be removed as soon as possible.

The U.S. Census Bureau estimates there are 76.4 million baby boomers, and the oldest of this generation, which includes those born between 1946 and 1964, are over 65 years old. For many of these people, adult diapers are a way to ameliorate the effects of moderate to severe incontinence. Adult diapers are a $7 billion global market, and sales have grown more than 8 percent over the past five years due to this increasing number of baby boomers entering their 70s and 80s. This trend appears to be rising as the stigma of wearing protective undergarments becomes less and the popularity of these products grow.

However, for males, particularly invalid males, diapers can be an unsatisfactory solution for several reasons. First, the previously raised issue that, once soiled, the patient must be changed like an infant by a caregiver who may not have the strength to lift a full grown adult male. Changing a diaper can lead to the patient being moved in positions that may strain or injure the patient, particularly when moved by a caregiver with inadequate strength to properly maneuver a full grown adult male. Second, unlike females where the origin and direction of the urine stream is fairly predictable, males tend to urinate from different positions, angles, and directions, and this inconsistency leads to leakage. This is especially true when the patient is lying on his back and suffers incontinence, because a gap in the top of the diaper at the patient's stomach can provide an opening where urine can leak outside of the diaper, leading to the issues raised above. Patients who go frequently can get ignored because of the challenges in changing the patient, leading to health issues as well.

The art is in need of a simple, cost effective device that is directed to the problem of male incontinence, and can reduce the opportunity for leakage as well as the frequency in which a patient needs to be moved when an incontinent event occurs. The present invention is directed to this objective.

SUMMARY OF THE INVENTION

The present invention is directed to a disposable urine trap in the form of a foldable pad that envelops the male genitalia and closes around the penis to form a barrier to prevent urine from escaping the trap. The pad includes an asymmetric pair of wings that are separated by a void attached to the main body of the pad. The first wing is preferably rectangular in that the distal angles are substantially right angles with parallel side edges and a perpendicular distal edge, and has a length that exceeds a length of a second wing, which is terminates so that the distal edge of the second wing is angled to form an obtuse and an acute angle with respect to its generally parallel sides. The void between the two wings may be formed by eliminating a triangular component from each inner side of the first and second wings to establish a "kite" or "diamond"-shaped void in the pad. The void in the pad may receive the patient's penis at its base such that the penis extends over the widest and thickest portion of the pad and the head of the penis occupies the middle area of the pad. Once the pad is arranged so that the penis is laid over the pad through the void, the first wing is folded over the top of the penis along a crease where the void lies to overlay the penis and sandwich the penis between the pad and the first wing. The angle that the first wing protrudes away from the pad is selected so that the inner side edge of the first wing aligns with a proximal edge of the second wing when folded over penis as described above. The folding of the first wing closes the void so that the void now encircles the base of the penis as the penis lays on the pad. Once the inner side edge of the first wing is placed against the proximal edge of the second wing, the second wing is then folded over the first wing such that the distal edge of the first wing and the distal edge of the second wing are substantially orthogonal. The asymmetric nature of the first and second wings allow the configuration described above, such that the wings cooperate to overlay the penis can capture the penis between the two wings and the thick portion of the pad. An adhesive strip on the opposite side of the first wing attaches to the second wing and secures the urine trap in the closed configuration. The corners of the pad can then be folded over the outer side edges of the adjacent first and second wings to close the trap and envelope the penis inside the pad.

A benefit of the present invention is that it can be placed inside a diaper as well as an undergarment. If a male patient should urinate in the urine trap, a caregiver can simply remove the urine trap from the diaper or undergarment without the need to undress, change the diaper, or move the patient. A new urine trap can be placed on the patient with little or no disturbance to the patient and without rolling the patient over, lifting the patient, or undressing the patient. Moreover, the configuration of the urine trap prevents any opportunity for leakage at the patient's waistline where most diapers can leak for male wearers because of the way the present invention envelopes the penis and the way the corners fold over the pad to eliminate gaps.

DETAILED DESCRIPTION OF THE PREFERRED EMBODIMENTS

Figure 1:
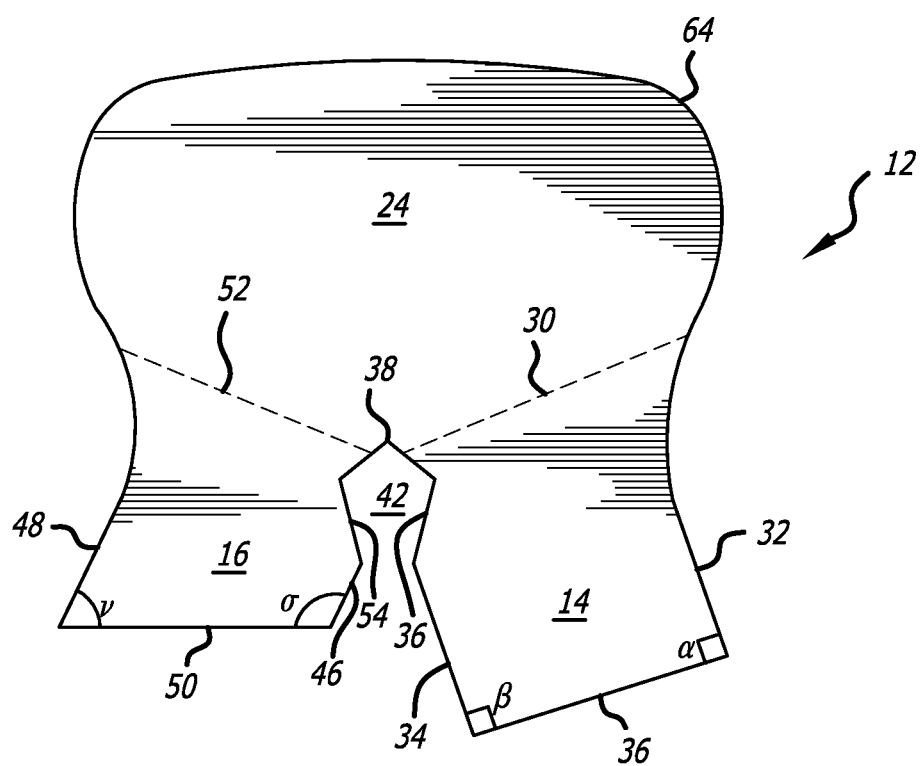
FIG. 1 is a top view of a first preferred embodiment of the present invention.

FIG. 1 illustrates a plan view of a first preferred embodiment of the present invention, comprising a pad 12 generally formed by a base 24 and first and second wings 14, 16. The pad 12 is formed by enclosing fluid absorbent material between an fluid impervious outer lining 18 and a soft fluid transmissive inner lining 20. The outer lining 18 may be made of a polyethylene film or other low cost, biocompatible material to seal in the urine and prevent leakage outside of the trap. The inner lining 20 that bear's against the user's skin may be made of polypropylene or suitable non-abrasive, non-toxic material that transmits fluid while largely staying relatively fluid free at the surface. The absorbent center 22 may contain wood pulp and super-absorbent polymers such as sodium polyacrylate. Sodium polyacrylate is effective in wicking away fluid from the skin through the inner lining 20, and can soak up to 30 times its weight in urine. The absorbent center is bordered around its edges by adhering the inner lining 20 and outer lining 18, and the matching of the two mating linings 18,20 can be arranged to give the pad a rounded shape in the undeformed condition. That is, a shallow "bowl" or saucer is created by the fit of the two mating edges such that the edges of the pad are raised with respect to the base 24. The base 24 is particularly padded at this middle portion, which is where the introduction of urine is expected in most cases.

As further seen in FIG. 1, a first elongated wing 14 extends distally from a crease 30. The first wing 14 is elongated and includes an outer side edge 32, an inner side edge 34, and a distal edge 36. The side edges 32,34 are substantially parallel, and the distal edge substantially perpendicular thereto, such that right angles $\alpha,\beta$ are formed. A generally triangular portion 36 of the inner edge 34 is removed at the juncture 38 of the first and second wings 14, 16, creating half of a void 42 through which the penis 76 is inserted.

An elongated second wing 16, which in a preferred embodiment has a length that is approximately one half a length of the first wing 14, protrudes distally to from a crease 52 and includes an inner side edge 46, outer side edge 48, and distal edge 50. As with the first wing, the inner side edge 46 and outer side edge 48 are substantially parallel, but the distal edge 50 forms an acute angle v with the outer side edge 48 and an obtuse angle α with the inner side edge 46. A triangular portion 54 of the inner edge 46 is removed at the juncture 38 of the first and second wings 14, 16, creating the other half of the void 42, which is thusly formed in a shape of a diamond based on the two triangular resections 36,54 on the inner edges 34, 46 to define an opening.

Figure 2:
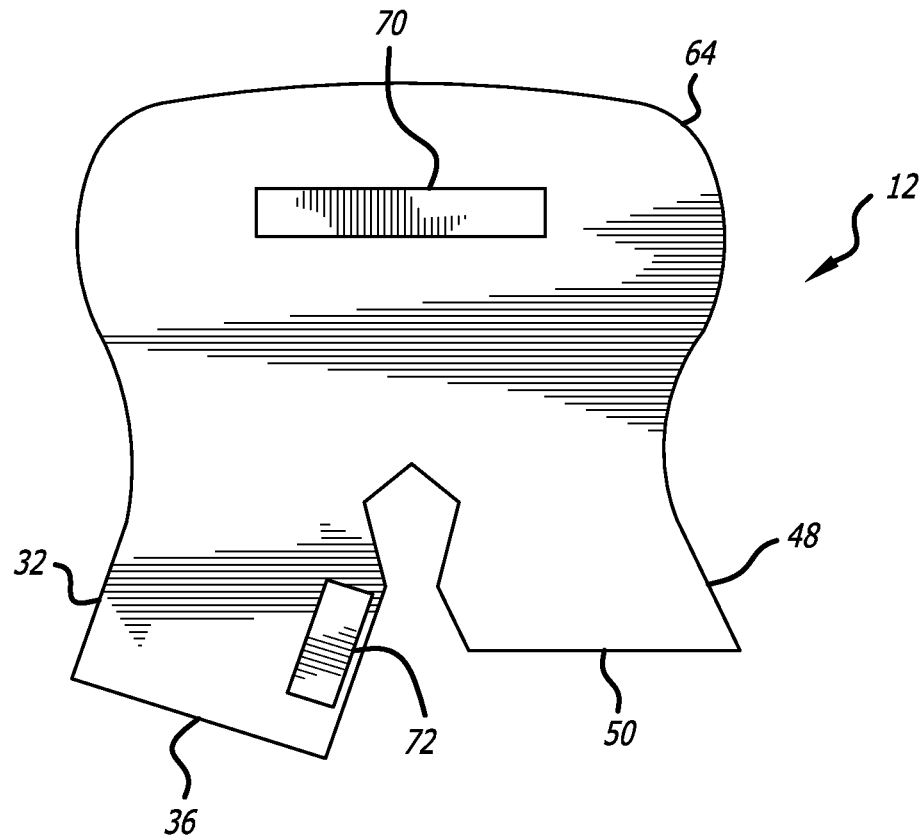
FIG. 2 is a bottom view of a the embodiment of FIG. 1.
Figure 3:
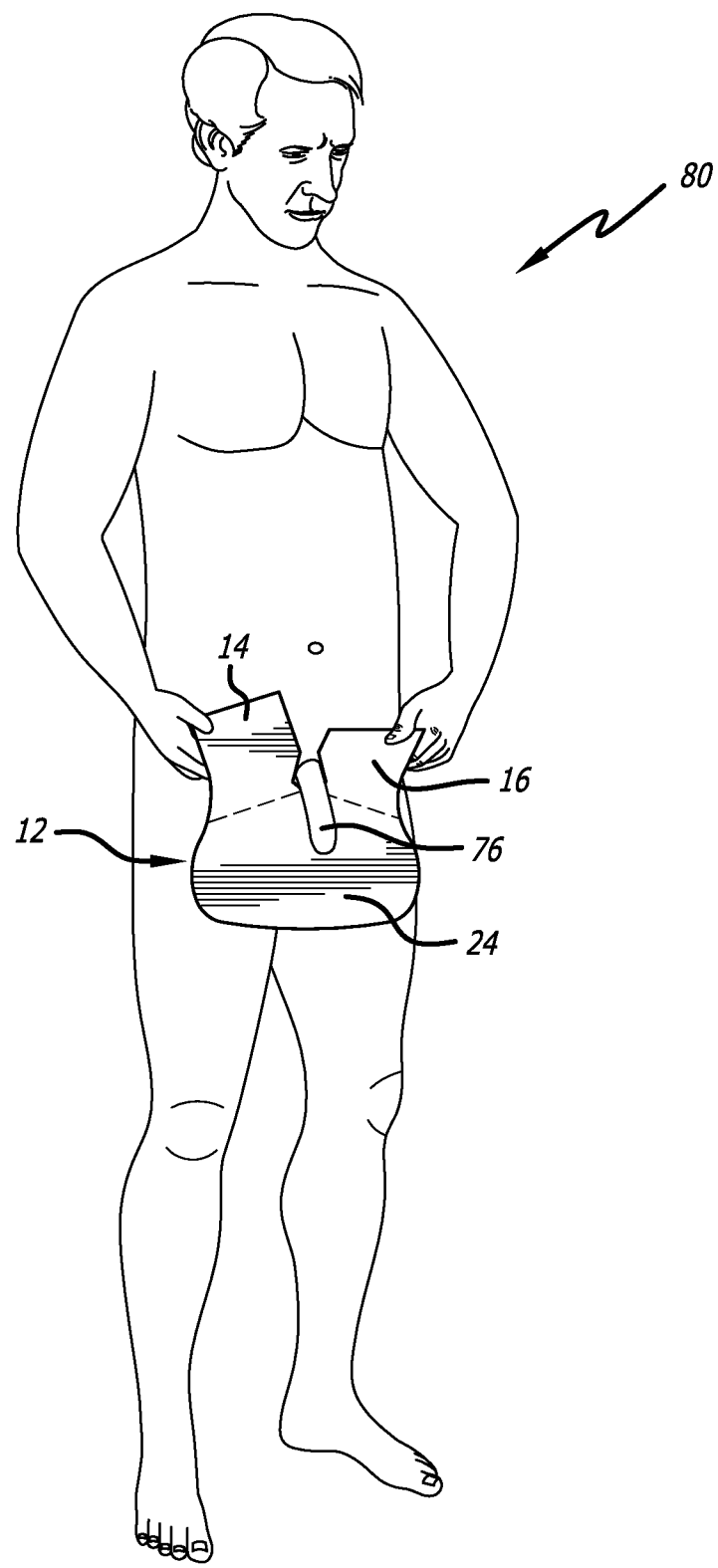
FIG. 3 is an elevated, perspective view of the present invention shown on a male user.

FIG. 2 illustrates a rear view of the pad 12, including a peel away adhesive strip 70 that can be used to secure the pad to the patient or a waistband of the patient. A second adhesive strip 72 is used to hold the pad in a pouch, or folded position to envelope the patient's genitalia 76.

Figure 4:
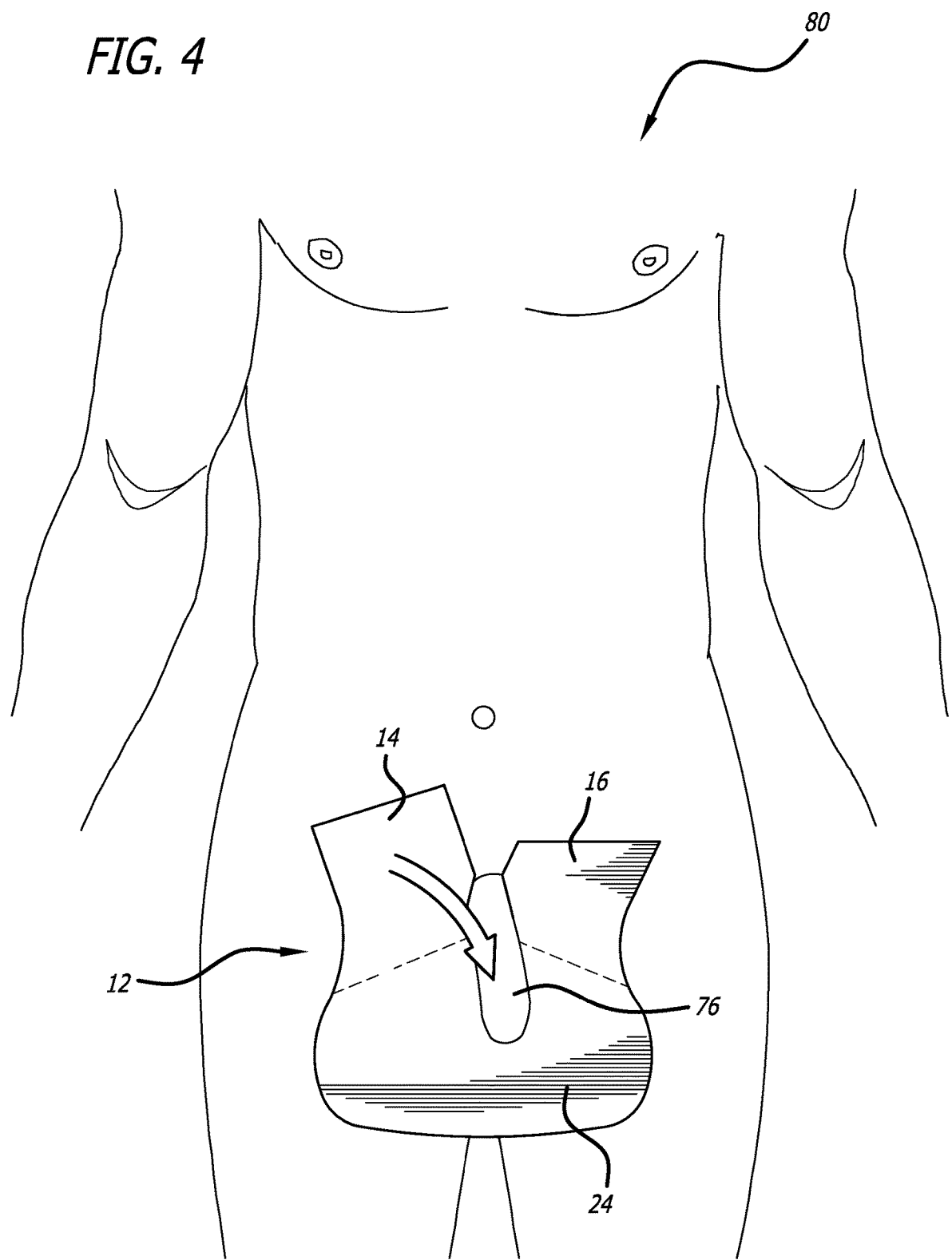
FIG. 4 is an enlarged, perspective view of the present invention.
Figure 5:
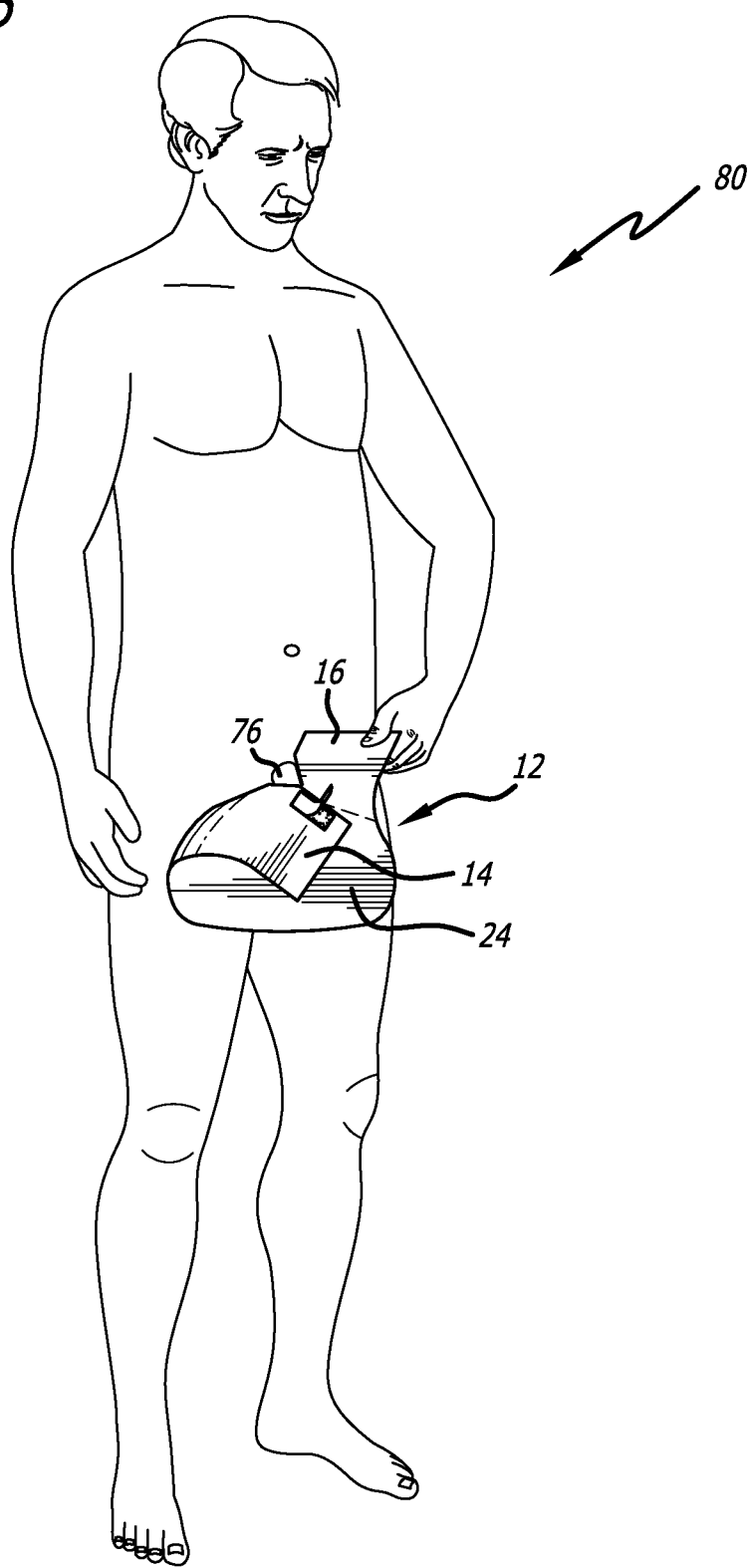
FIG. 5 is an elevated, perspective view of the present invention with the first wing folded.
Figure 6:
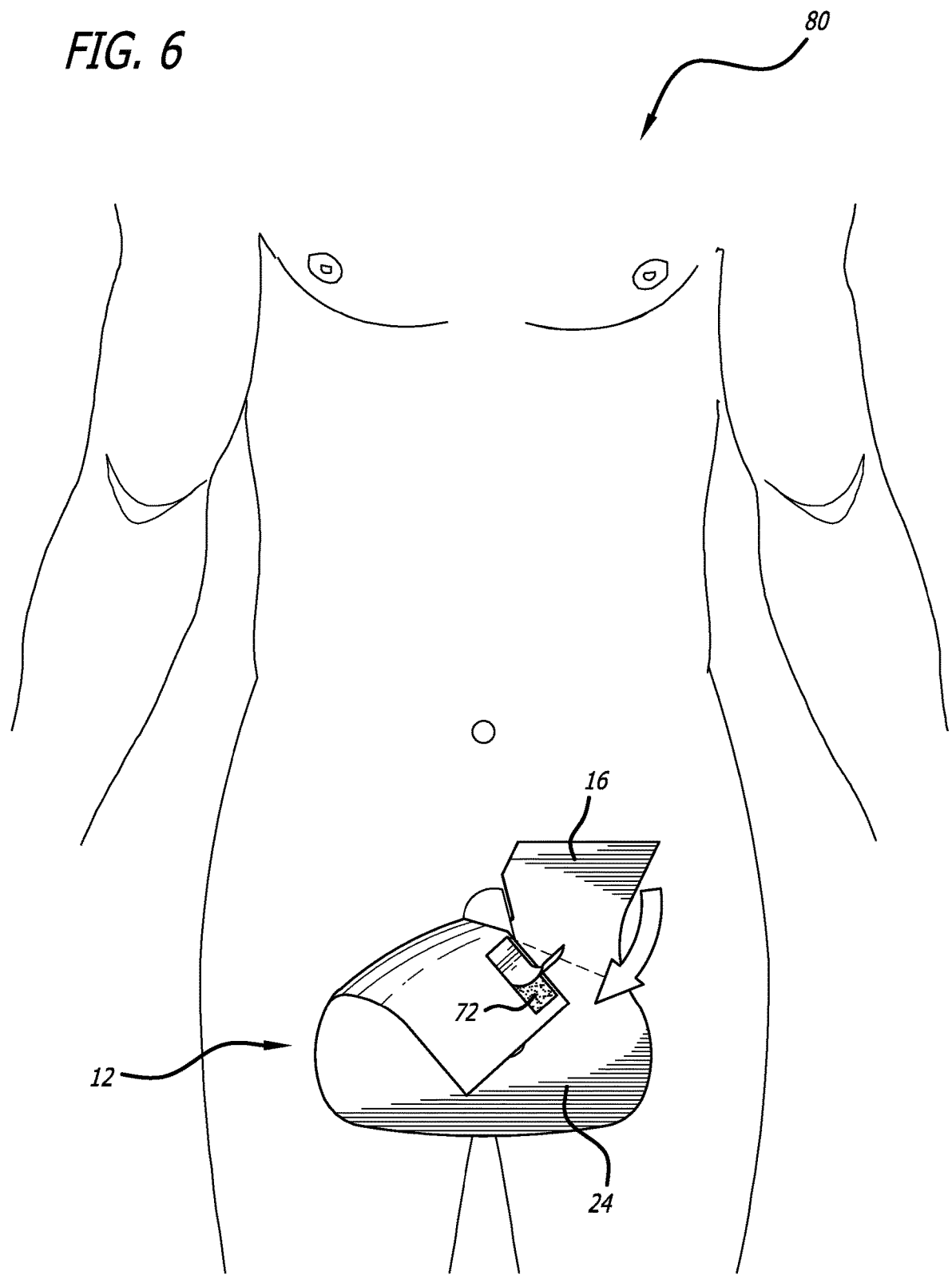
FIG. 6 is an enlarged, perspective view of the present invention with the adhesive strip removed.
Figure 7:
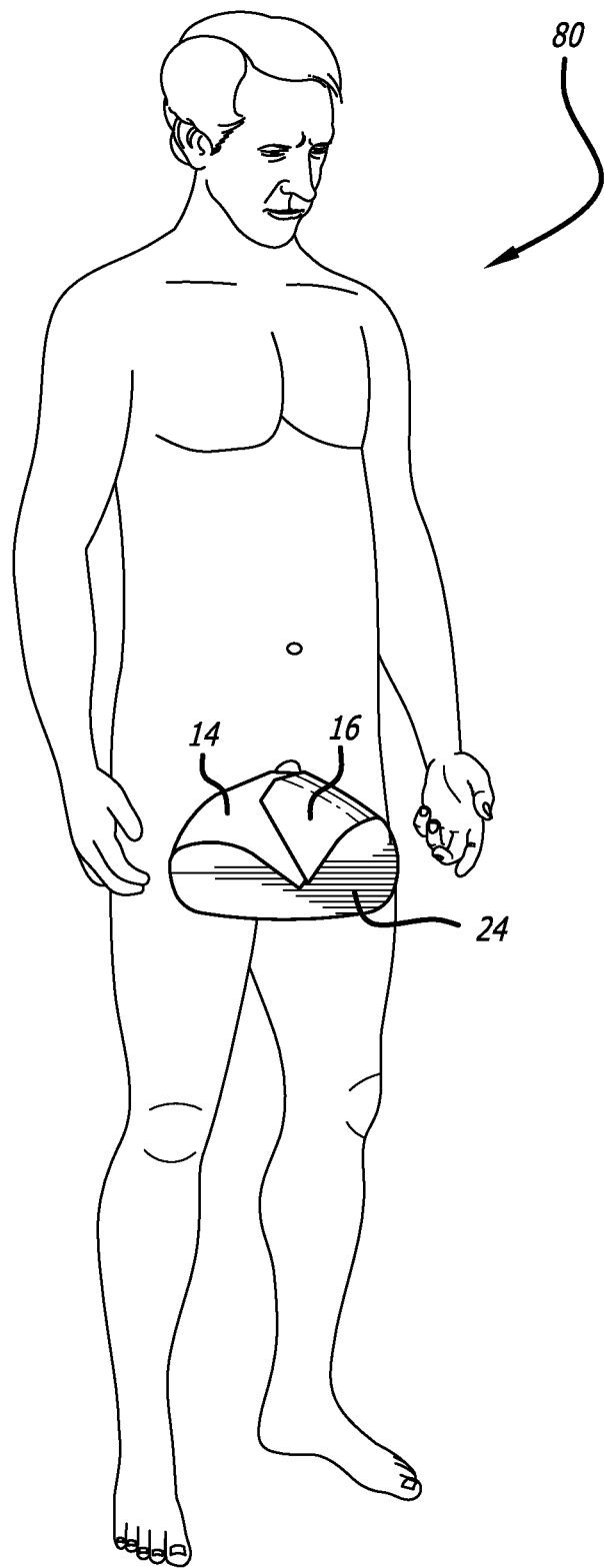
FIG. 7 is a perspective view of the second wing folded into place.
Figure 8:
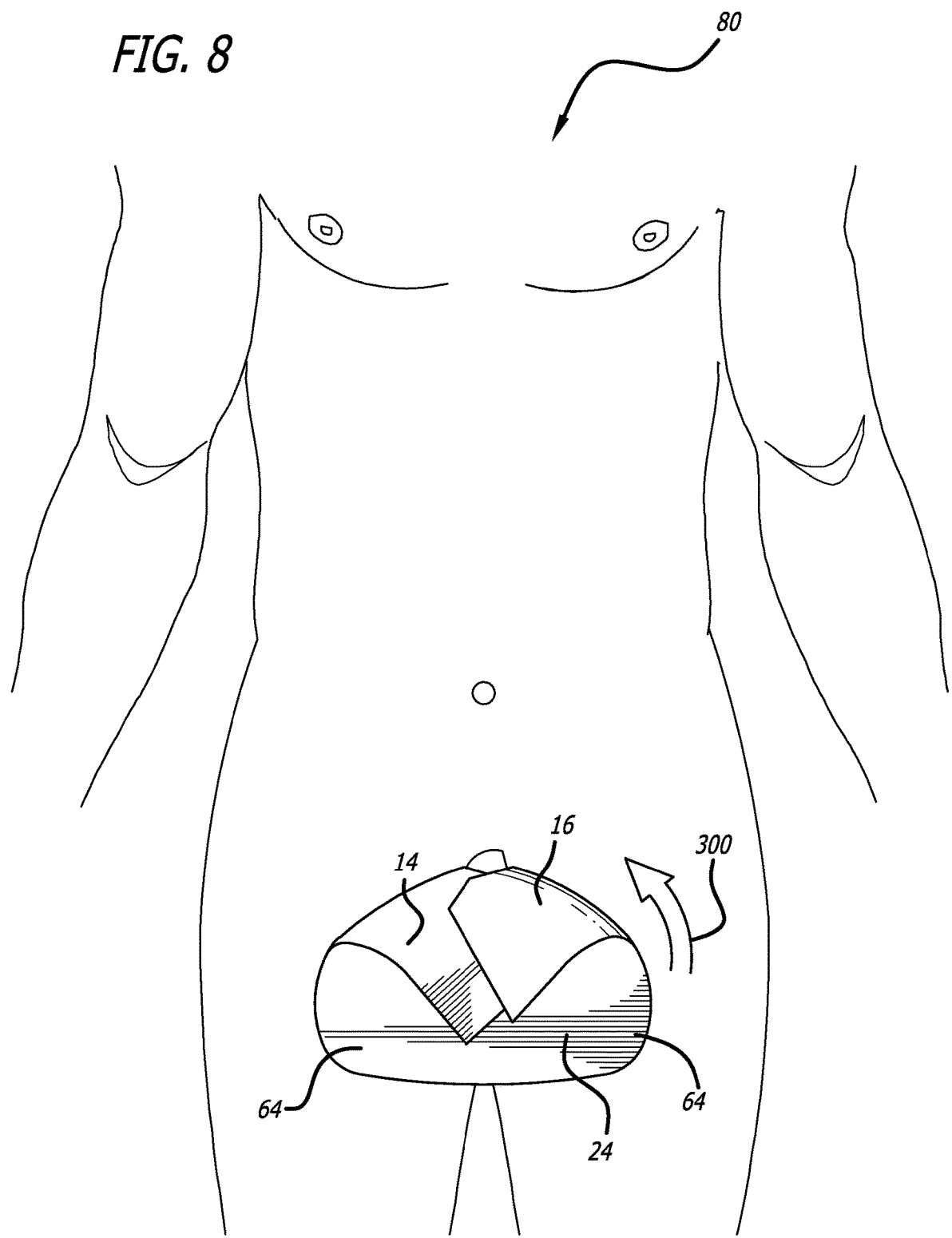
FIG. 8 is an enlarged, perspective view of corners being upturned to enclose the male genitalia.

FIGS. 3-13 illustrate a first method for how the pad 12 encloses the male organ and creates a cocoon-like conically shaped wrap around the organ to collect any urine and prevent leakage. With the patient 80 preferably standing or lying on his back, the pad 12 is placed on the user's thighs with the first wing 14 on the upper right thigh/abdomen and the second wing 16 over the user's left thigh/abdomen. The user's penis 76 is placed in the void 42 between the first and second wings 14,16 so that the base of the penis is at the juncture 38 and the head of the penis is in the central portion, or base 24 of the pad 12 (FIG. 4). The first wing 14 is then folded along crease 30 over the top of the penis such that the inner side edge 34 is approximately along crease 52 (FIGS. 4, 5). The placement of the first wing 14 in this position covers the penis 76, and exposes the adhesive strip 72 adjacent the second wing 16. The protective cover is removed from the adhesive strip 72 (FIG. 6), and the second wing 16 is then folded at crease 52 over the first wing 14 such that the distal edge 50 is approximately parallel to and adjacent to the side outer edge 32 of the first wing 14 (FIG. 7). This configuration encloses the penis 76 in the opening void 42 and creates a leak-proof pouch over the penis. The first and second wings 14, 16 overlap and cooperate to form a "V" over the penis (FIG. 8), and the corners 64 can then be folded over the "V" in the direction of arrow 300 (FIG. 8) to close the pouch like an envelope, eliminating any opportunity for urine to escape during urination. A double layer of protection created by the wings 14, 16 (FIGS. 12 and 13) reduce the opportunity for leakage and create a drier, more moisture-free environment for the user 80. As shown in FIG. 1, the first wing 14 is constructed with an area over 40% of that of the main region 24.

Figure 9:
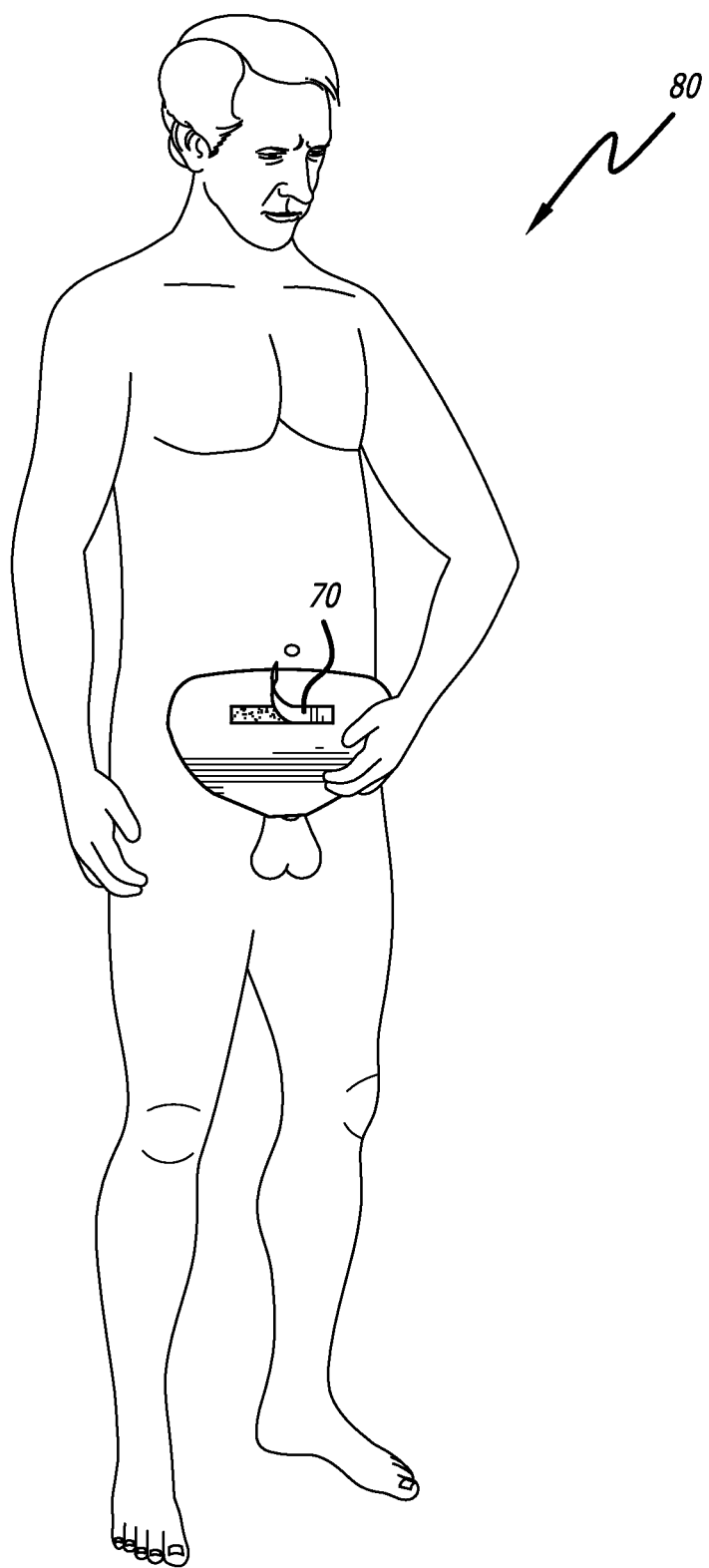
FIG. 9 is an elevated, perspective view of the adhesive strip being removed so as to be applied to a garment.
Figure 10:
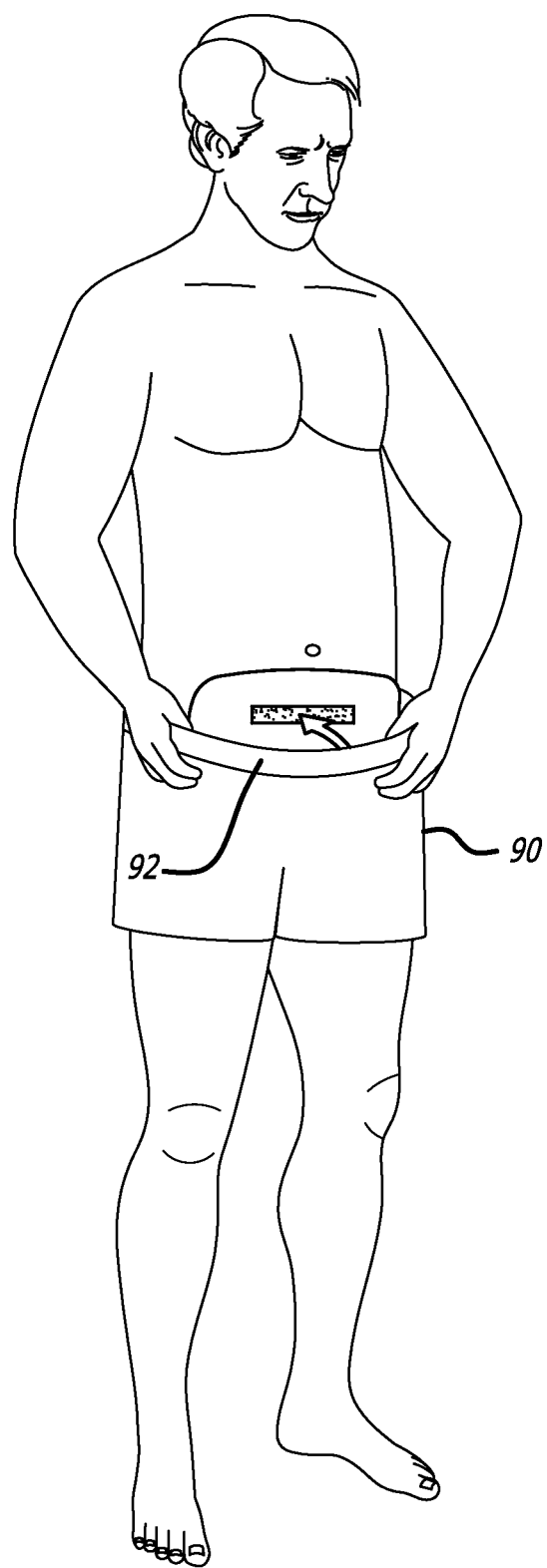
FIG. 10 is an elevated, perspective view of the pouch adhered to an undergarment.
Figure 11:
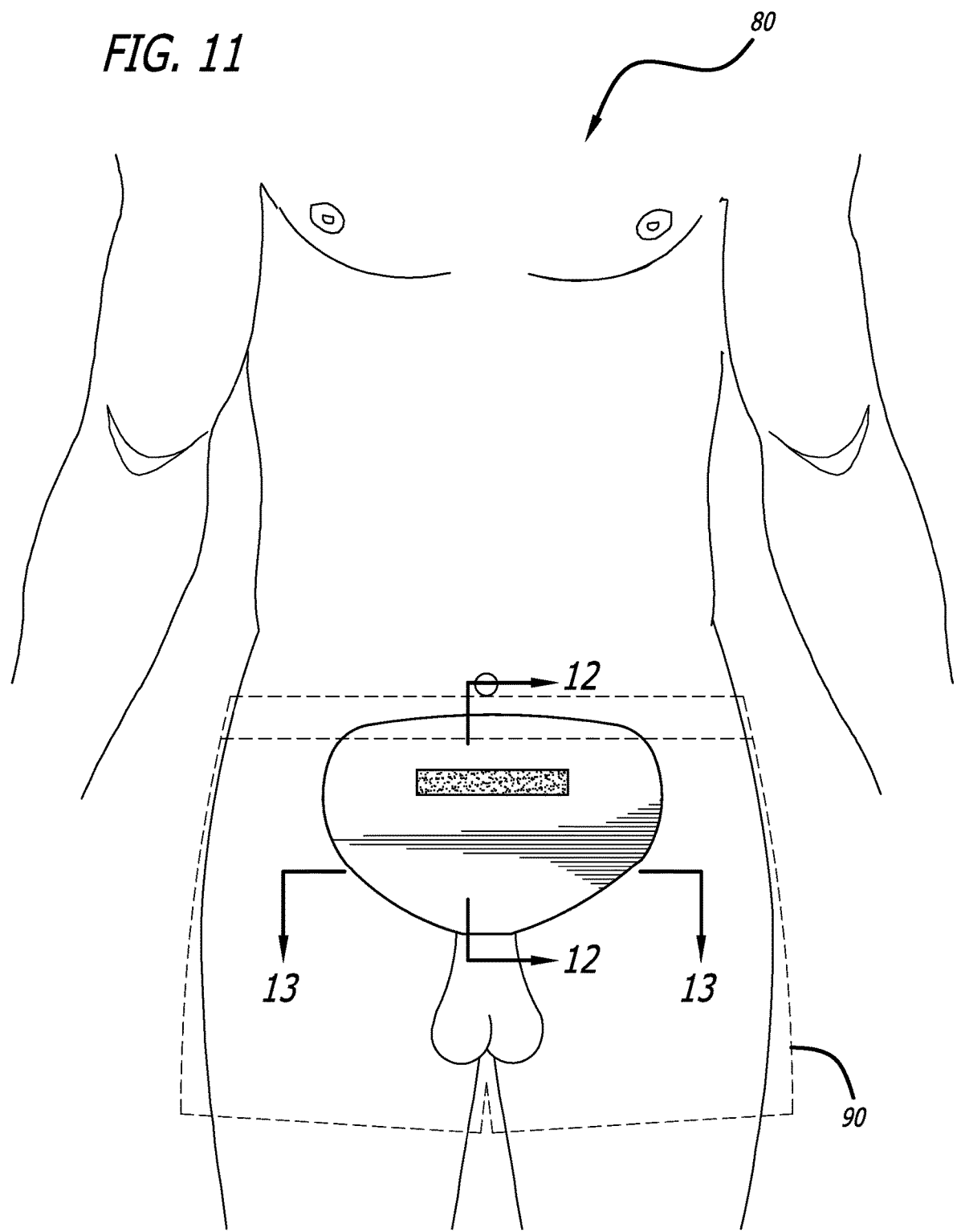
FIG. 11 is an enlarged, perspective view partially in shadow showing the pouch in place inside an undergarment.
Figure 12:
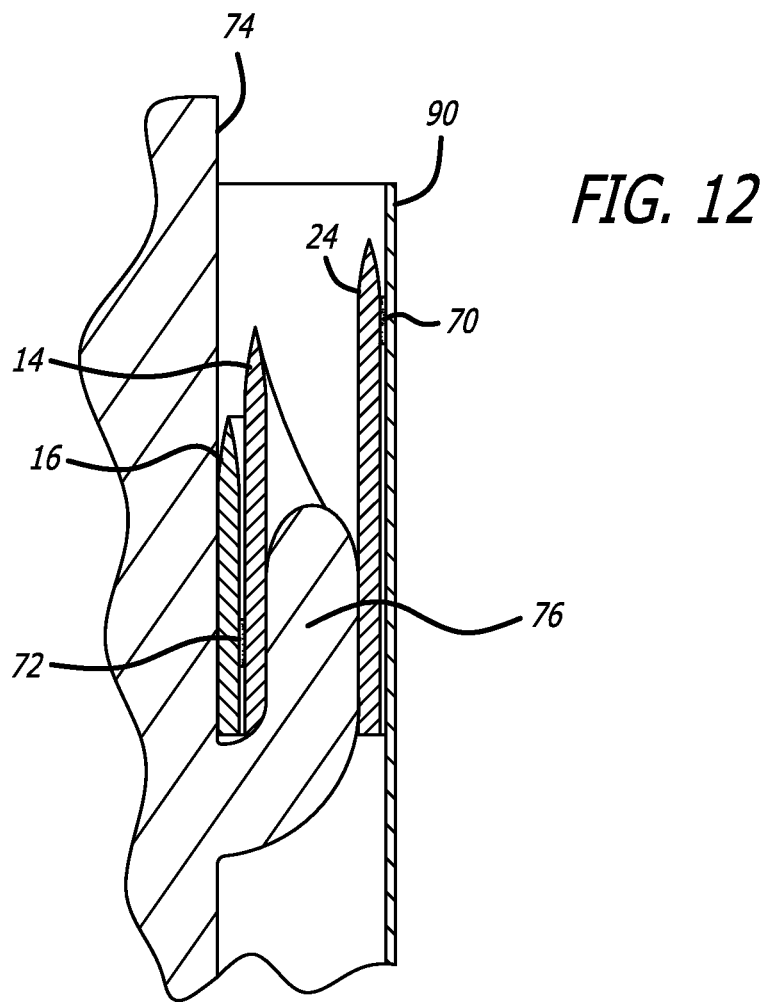
FIG. 12 is a first cross sectional view of the pad in the pouch configuration.
Figure 13:
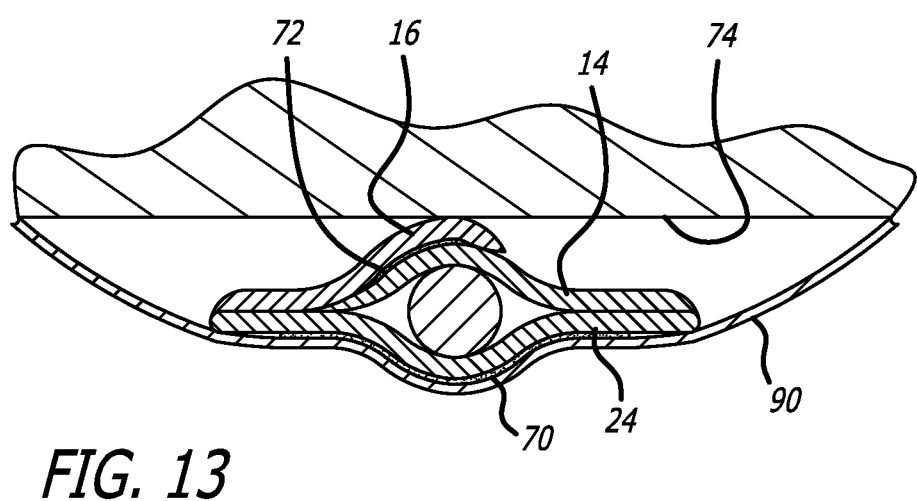
FIG. 13 is a second cross sectional view of the pad in the pouch configuration.
Figure 14:
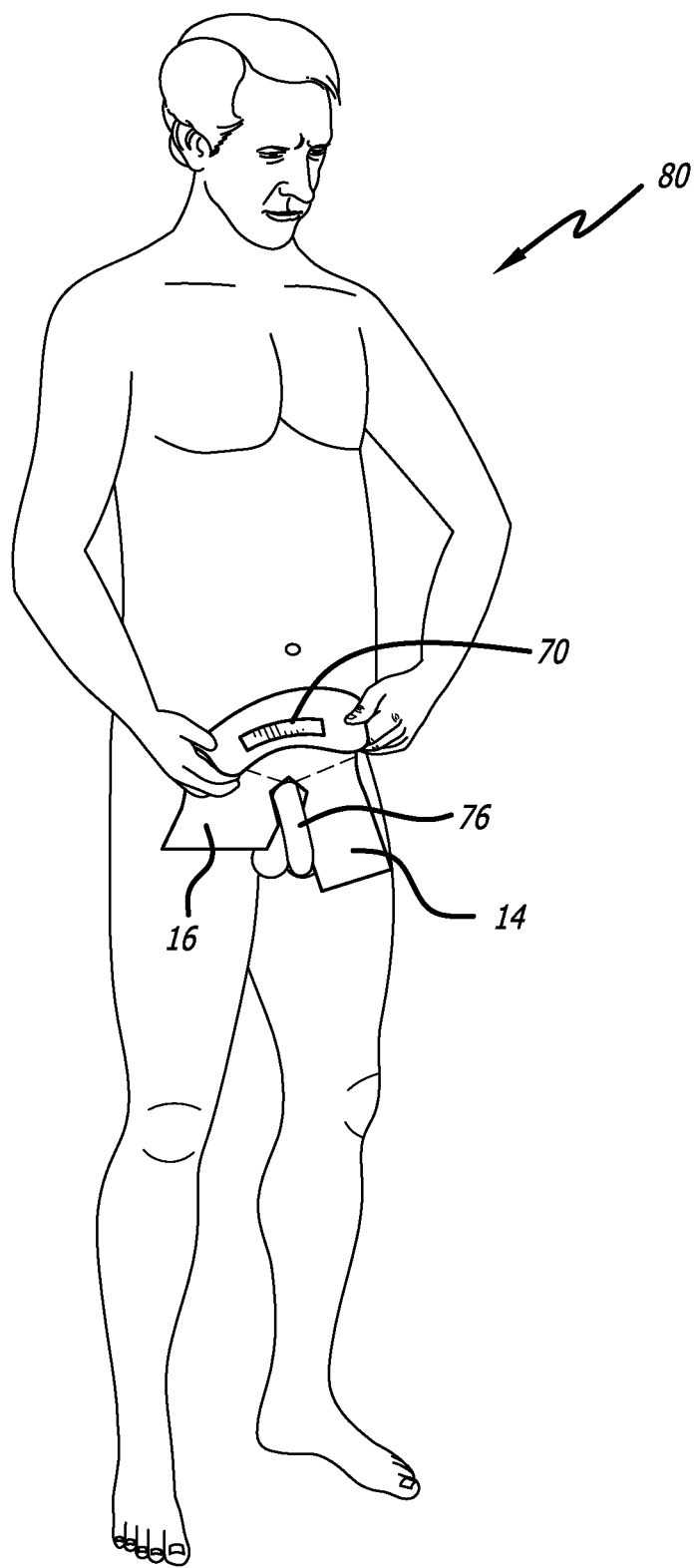
FIGS. 14-23 illustrate an alternate way of wearing the pad of the present invention.
Figure 15:
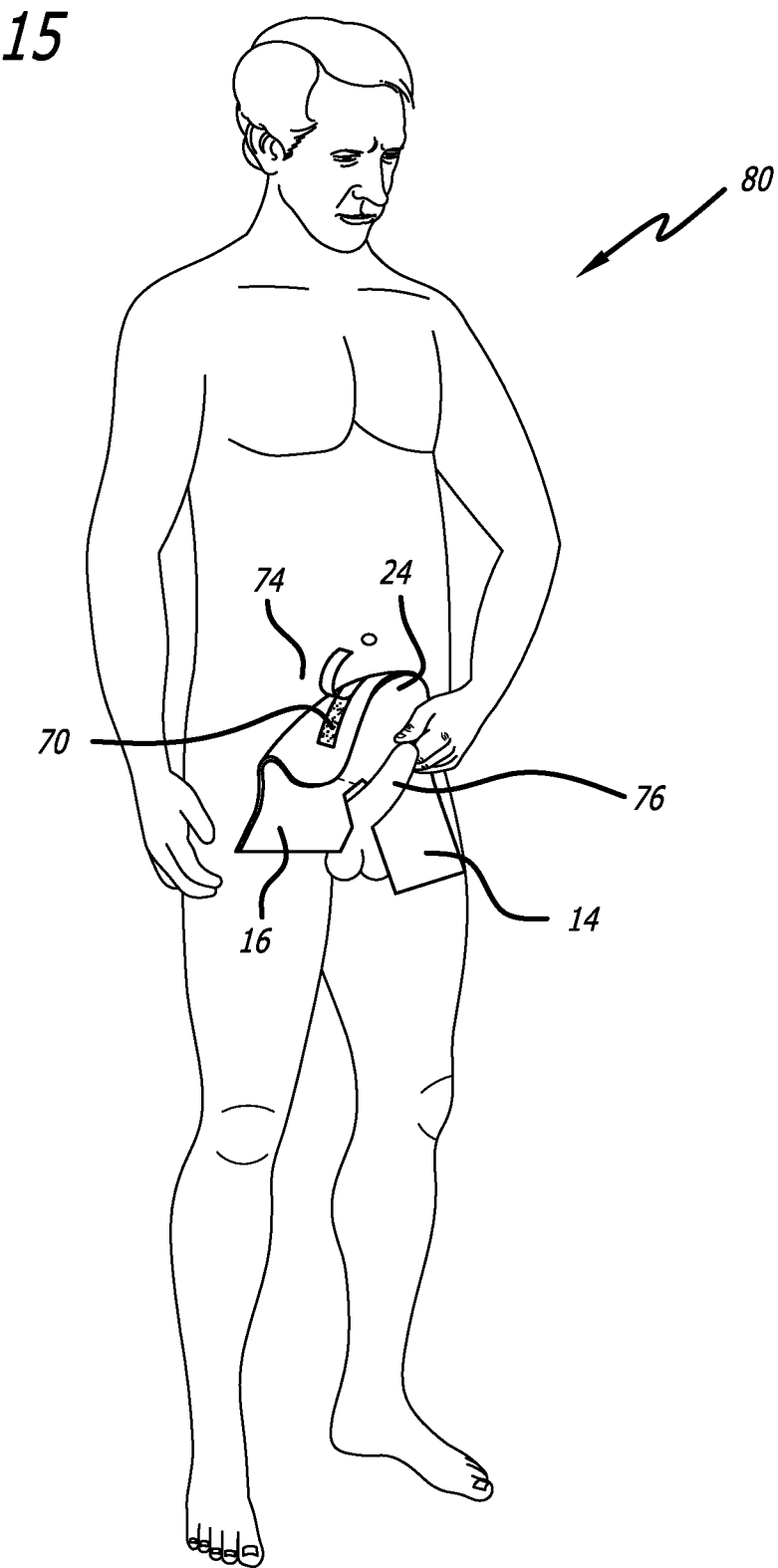
Figure 16:
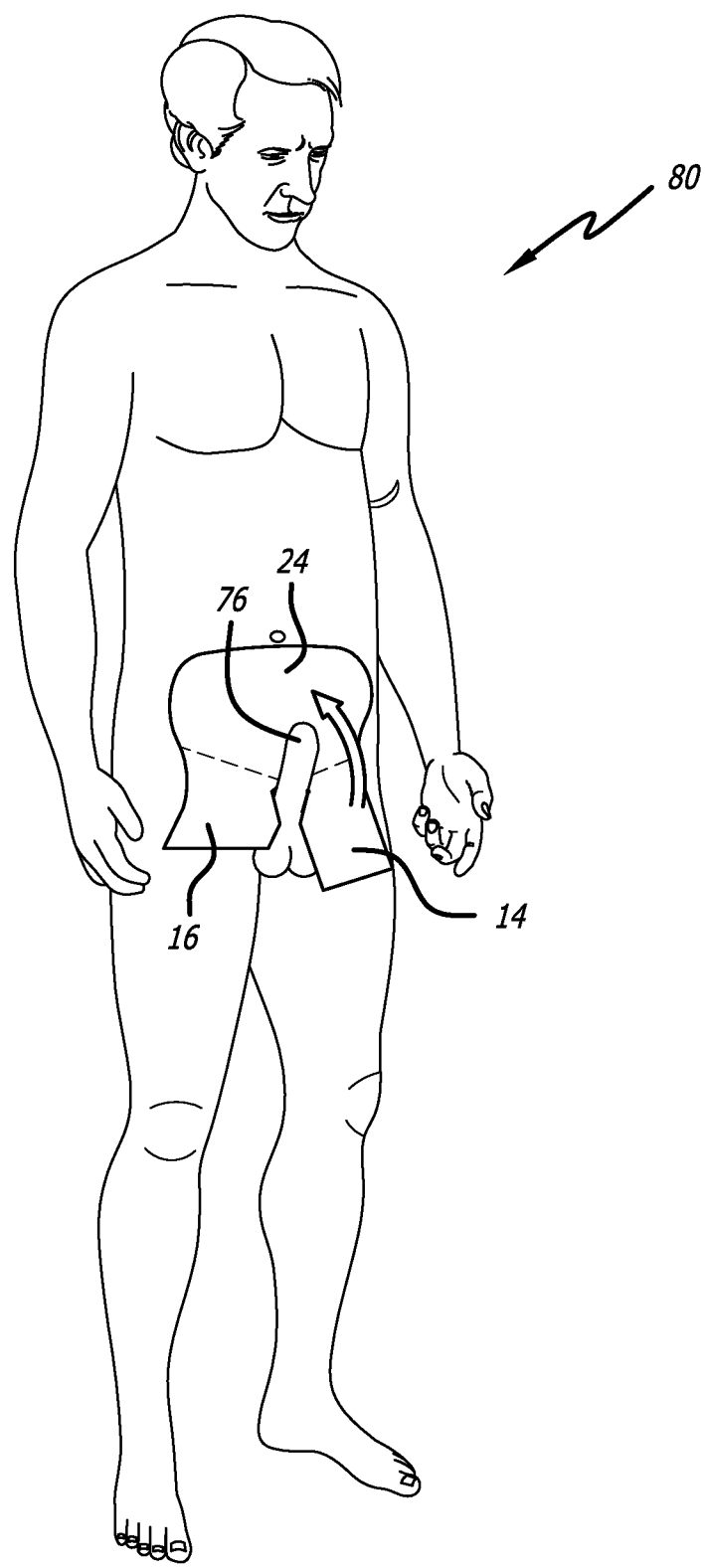
Figure 17:
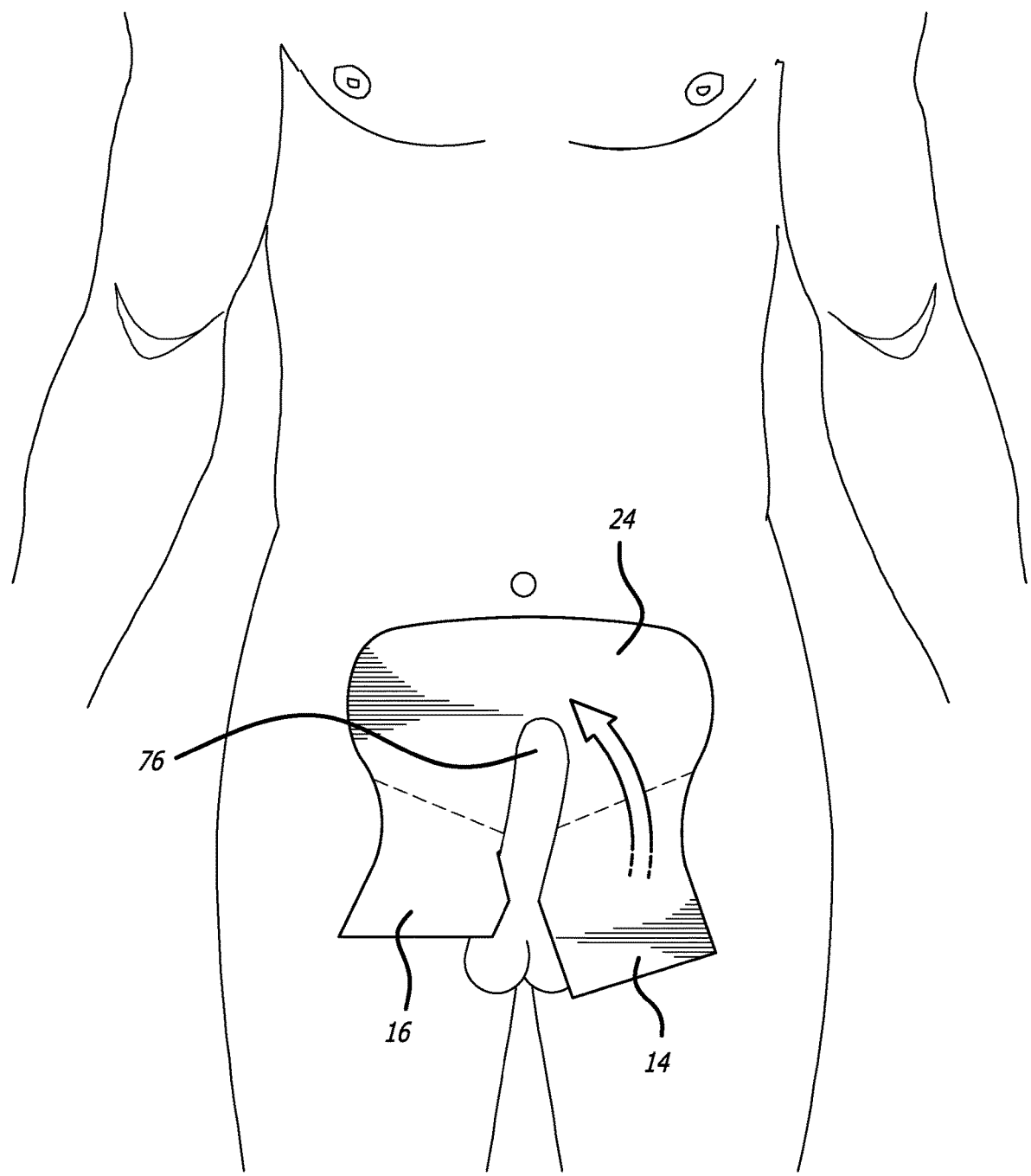
Figure 18:
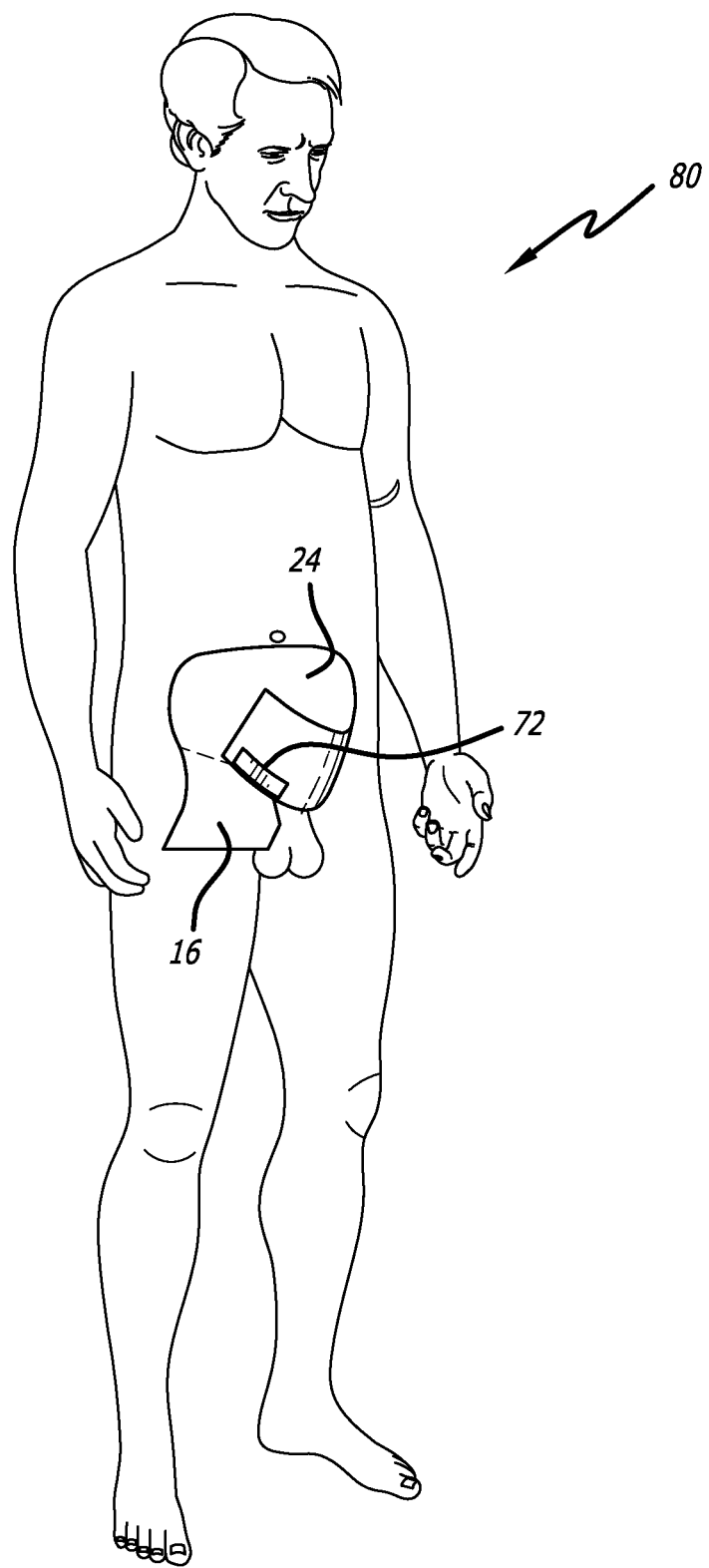
Figure 19:
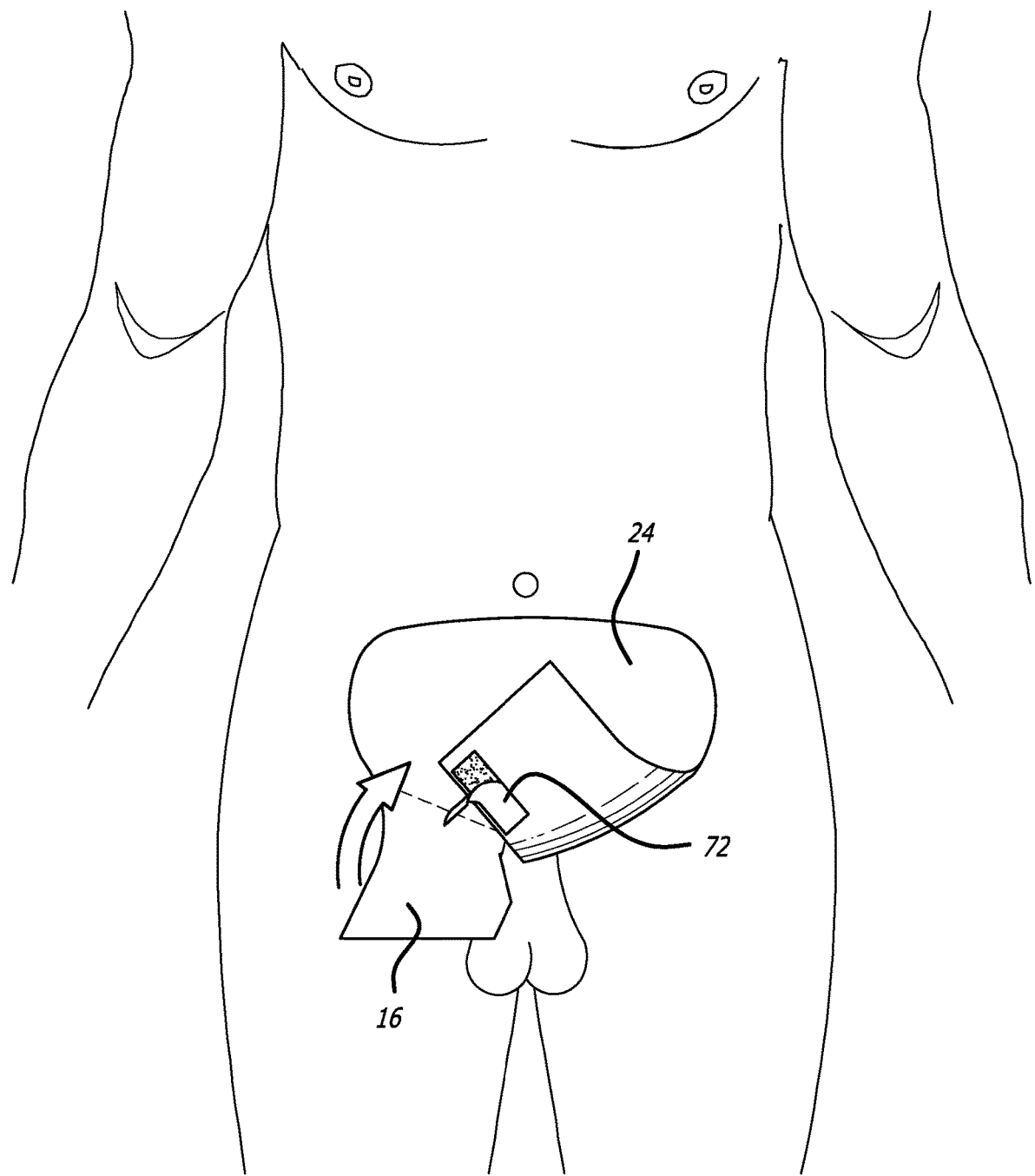
Figure 20:
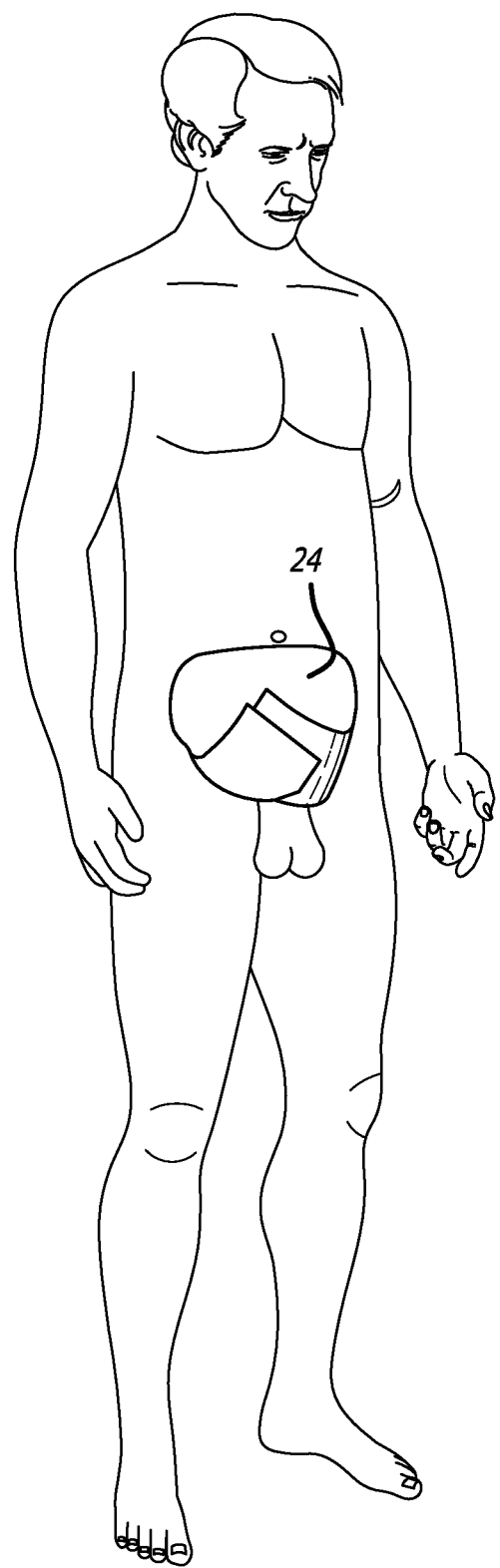
Figure 21:
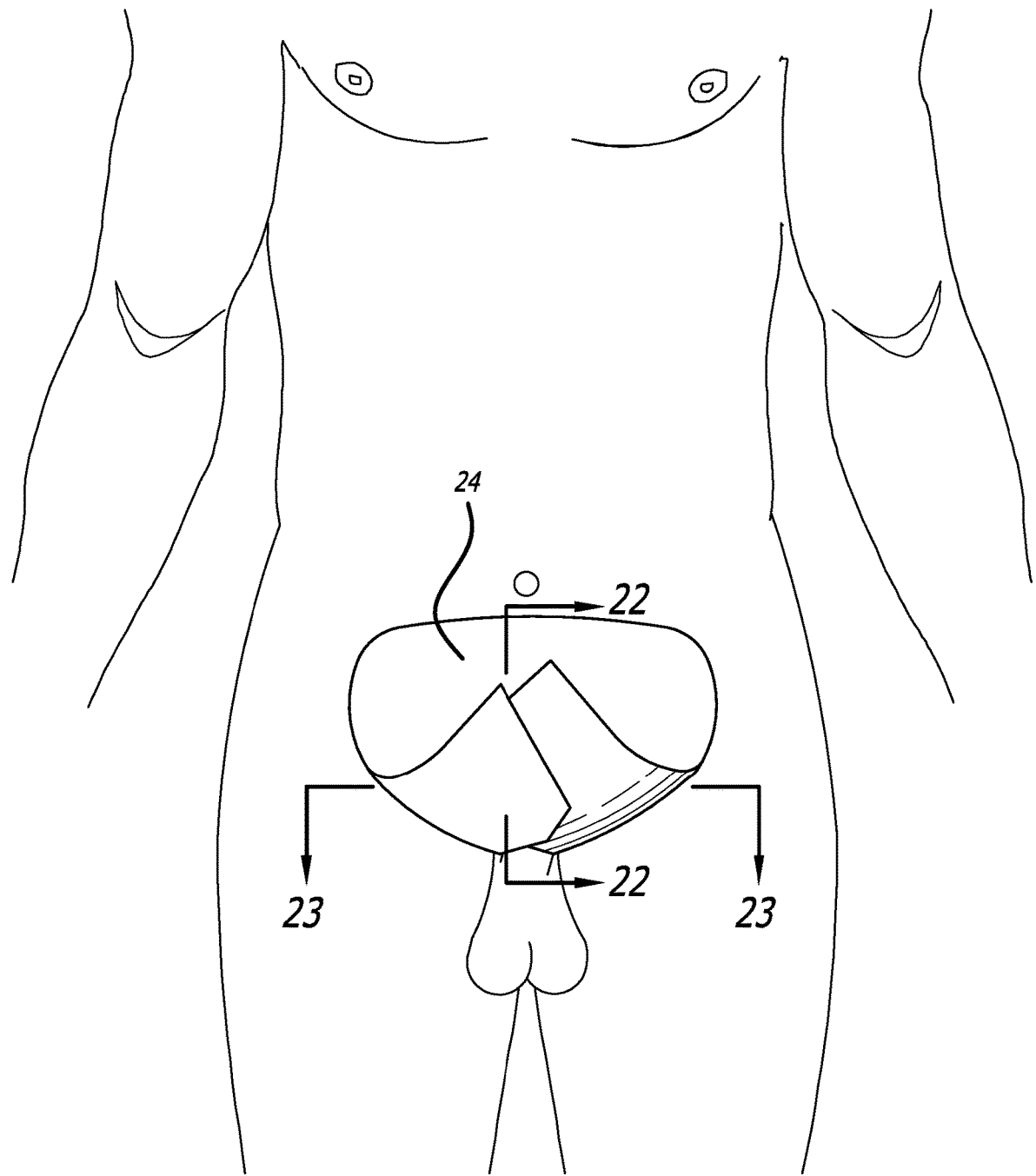
Figure 22:
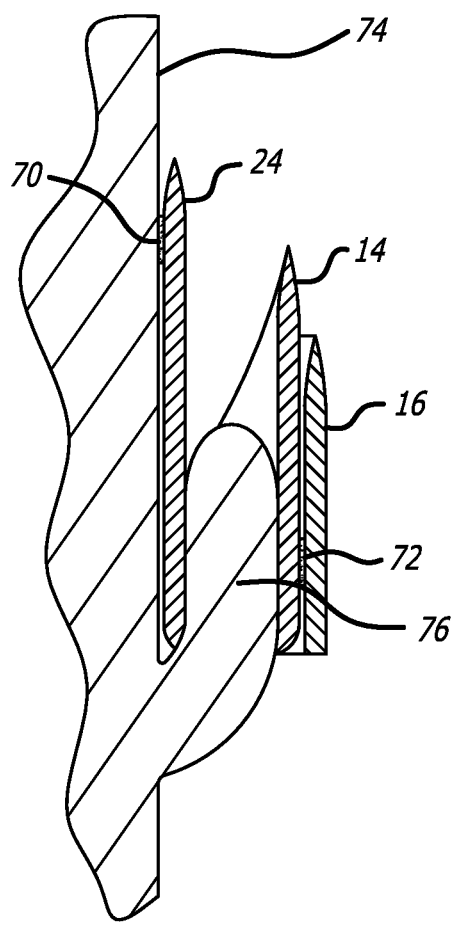
Figure 23:
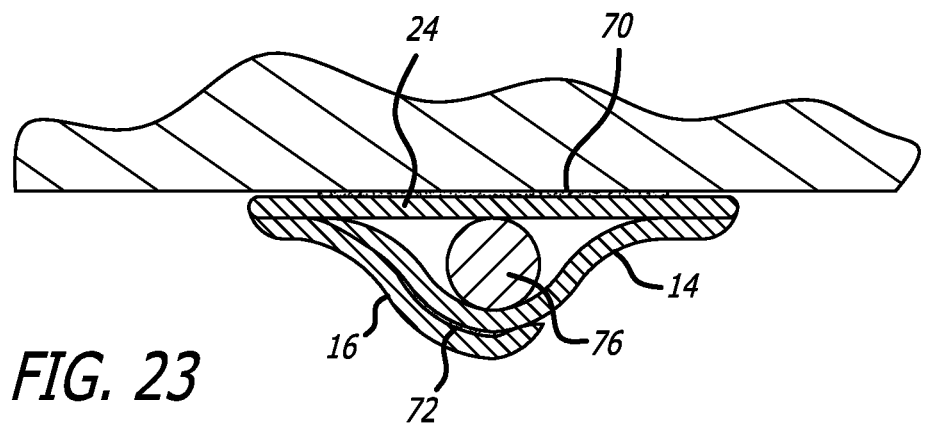

As shown in FIGS. 9-11, the urine trap 12 can be placed inside a diaper or underpants 90 of a patient 80 without the need to fully undress the patient. If the patient should have incontinence while wearing the urine trap, it can be removed easily and replaced by a new pad with minimal jostling or movement of the patient. The larger adhesive strip 70 can be placed on the backside of the pad to secure the pad to the patient's waistband 92 of his pants or underwear 90 to maintain the urine trap in position. Alternatively, a plurality of adhesive strips can be secured to the back side or front side of the urine trap to secure it to a gown or other more loose-fitting clothing.

The unique shape of the first and second wings have multiple benefits over the existing prior art. First, the wings minimize the amount of material needed to establish a secure and reliable pouch, and eliminate excess flaps that can catch on garments and inadvertently open the pouch. For example, the inner side edge 46 of the second wing 16 aligns with the base of the first wing 14 at the crease 30 when the second wing 16 is folded over the first wing 14. Similarly, the inner side edge 34 of the first wing 14 aligns perfectly with the base of the second wing 16 at the crease 52 when the first wing 14 is folded over the penis. The alignment of the inner edges against the opposite crease maximizes the volume of the pouch and eliminates excess wing material bunching up or contacting the penis. The novel shape aligns the edges of the wings to ends of the pouch itself, creating a perfectly formed and reliable pouch with no excess material. Second, cut-outs 36, 54 form a more comfortable opening through which the wearer's penis is secured, reducing chaffing and skin irritation. By eliminating all excess material, the user can wear the urine trap under regular clothes as well without large, bulky bulges that can be created by traditional diapers. A taped border may extend along the wings from the respective creases to ensure that the edges mate more smoothly and prevent gaps that can cause leakage.

In an alternative embodiment as shown in FIGS. 14-23, the pouch can be applied and worn in a reverse manner. Advantages may be seen in this configuration depending on whether the user is prone or ambulatory. The adhesive strip may be secured to the user 80 in this embodiment, wear only a gown or other loose fitting clothing are worn and there is nothing else to which one can apply the adhesive strip.

The foregoing description is intended to be illustrative and not exclusive. That is, there are many variations and modifications that can be made to the foregoing descriptions and preferred embodiments that would be readily apparent to one of ordinary skill in the art, and the present invention is intended to include all such modifications and variations. Such modifications may include choice of materials, overall dimensions of the embodiment, etc. Accordingly, the scope of the present invention should not be limited to any specific embodiment, illustration, or description herein, but rather the scope of the invention should be determined by the appended claims using the plain and ordinary meaning of the words used therein.

I claim:

1. A male urine trap, comprising:
an inner fluid transmissive layer, an absorbent layer, and a fluid impermeable layer forming a flexible pad, the pad including:
a main absorbent region;
first and second spaced apart wings depending from the main absorbent region, the first wing including an outer side edge, and inner side edge, and a distal edge, the inner side edge including a first triangular void adjacent a juncture of the first and second wings, and the second wing includes an inner side edge, an outer side edge, and a distal edge, where the distal edge forms an acute angle with the second wing's outer side edge and an obtuse angle with the second wing's inner side edge, and a second triangular void at the juncture of the first and second wings, where the first and second triangular voids form a diamond shaped recess;
an attachment for securing the second wing to the first wing; and
whereby a compartment is formed, between the main absorbent region and a combination of the first and second wings, by overlapping the first and second wings, the compartment having a first entrance through the diamond shaped recess, and an opening along adjacent coincident side surfaces of the folded first and second wings;
a waistband adhesive strip on the main absorbent region; and wherein the second wing is folded over the first wing and the distal edge of the second wing is parallel to and adjacent the outer side edge of the first wing, and wherein the main absorbent region is folded over the distal edges of the first and second wings.

\* \* \* \* \*